United States Patent
Silva et al.

(10) Patent No.: US 11,534,752 B2
(45) Date of Patent: Dec. 27, 2022

(54) RAPID TEST DEVICE HAVING MULTIPLE HETEROGENEOUS DIAGNOSTIC METHODS

(71) Applicant: International Business Machines Corporation, Armonk, NY (US)

(72) Inventors: Ademir Ferreira da Silva, Sao Paulo (BR); Jaione Tirapu Azpiroz, Rio de Janeiro (BR); Matheus Esteves Ferreira, Rio de Janeiro (BR); Mathias B Steiner, Rio de Janeiro (BR); Daniel Vitor Lopes Marcondes Marçal, Rio de Janeiro (BR)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 164 days.

(21) Appl. No.: 17/138,419

(22) Filed: Dec. 30, 2020

(65) Prior Publication Data

US 2022/0203353 A1 Jun. 30, 2022

(51) Int. Cl.
*B01L 3/00* (2006.01)
*G01N 21/78* (2006.01)
*G01N 33/543* (2006.01)
*G01N 21/77* (2006.01)

(52) U.S. Cl.
CPC ............ *B01L 3/5023* (2013.01); *G01N 21/78* (2013.01); *G01N 33/54386* (2013.01);
(Continued)

(58) Field of Classification Search
CPC ............... B01L 3/5023; B01L 2200/10; B01L 2300/021; B01L 2300/023;
(Continued)

(56) References Cited

U.S. PATENT DOCUMENTS

| 10,807,087 B2 | 10/2020 | Jukka-Tapani |
| 2004/0115795 A1 | 6/2004 | Rees |

(Continued)

FOREIGN PATENT DOCUMENTS

| CN | 101528350 A | 9/2009 |
| CN | 203479805 U | 3/2014 |

(Continued)

OTHER PUBLICATIONS

Chinnasamy et al., A lateral flow paper microarray for rapid allergy point of care diagnostics, Mar. 5, 2014.
(Continued)

*Primary Examiner* — Jennifer Wecker
*Assistant Examiner* — Alea N. Martin
(74) *Attorney, Agent, or Firm* — Garg Law Firm, PLLC; Rakesh Garg; Joseph Petrokaitis

(57) ABSTRACT

An embodiment includes a sample receiving region, a first diagnostic element that includes one or more colorimetric analysis regions, and a second diagnostic element that includes one or more lateral flow assay analysis regions. The embodiment also includes a first flow path that allows a portion of a liquid deposited at the sample receiving region to flow to the first diagnostic element. The embodiment also includes a second flow path that allows a portion of the liquid deposited at the sample receiving region to flow to the second diagnostic element.

6 Claims, 13 Drawing Sheets

(52) U.S. Cl.
CPC ..... *B01L 2200/10* (2013.01); *B01L 2300/021* (2013.01); *B01L 2300/023* (2013.01); *B01L 2300/025* (2013.01); *B01L 2300/0864* (2013.01); *B01L 2300/165* (2013.01); *G01N 2021/7763* (2013.01)

(58) Field of Classification Search
CPC ....... B01L 2300/025; B01L 2300/0864; B01L 2300/165; G01N 21/78; G01N 33/54386; G01N 2021/7763
See application file for complete search history.

(56) References Cited

U.S. PATENT DOCUMENTS

| | | | |
|---|---|---|---|
| 2015/0111216 A1* | 4/2015 | Delahunt | B01L 3/5023 |
| | | | 435/6.15 |
| 2017/0219573 A1 | 8/2017 | Needham et al. | |
| 2019/0162717 A1 | 5/2019 | Mckee | |
| 2019/0302008 A1 | 10/2019 | Ohta et al. | |
| 2020/0282395 A1 | 9/2020 | Tirapu Azpiroz et al. | |
| 2020/0319158 A1 | 10/2020 | Gorewit | |
| 2020/0376485 A1 | 12/2020 | Azpiroz et al. | |
| 2020/0378957 A1 | 12/2020 | Azpiroz et al. | |

FOREIGN PATENT DOCUMENTS

| | | |
|---|---|---|
| CN | 107636460 A | 1/2018 |
| CN | 108351355 A | 7/2018 |
| CN | 111751525 A | 10/2020 |
| EP | 3717910 A1 | 10/2020 |
| HK | 1257991 A1 | 11/2019 |
| IN | 202017026424 A | 10/2020 |
| JP | 2010523996 A | 7/2010 |
| WO | 2017066645 A1 | 4/2017 |

OTHER PUBLICATIONS

Fenton et al., Multiplex Lateral-Flow Test Strips Fabricated by Two-Dimensional Shaping, vol. 1, No. 1, pp. 124-129, Nov. 24, 2008.

Martin-Hernandez et al., Immunochromatographic lateral-flow test strip for the rapid detection of added bovine Yennet whey in milk and milk powder, International Dairy Journal 19, Apr. 2009.

Li et al., Multiplex lateral flow detection and binary encoding enables a molecular colorimetric 7-segment display, Lab Chip, Nov. 24, 2015.

Zhu et al., A paper electrode integrated lateral flow immunosensor for quantitative analysis of oxidative stress induced DNA damage, Mar. 12, 2014.

Sheng et al., Visual and fluorometric lateral flow immunoassay combined with a dual-functional test mode for rapid determination of tetracycline antibiotics, Aug. 7, 2018.

LIC Automation, How it works, 2020.

Hoard's Dairyman, DeLaval Launches Innovative Somatic Cell Counting Device, Sep. 1, 2015.

Cappione et al., Rapid Counting of Somatic Cells in Dairy Milk Using the Scepter™ Cell Counter, Following Spin-Wash Sample Preparation, 2020.

Somaticell, Diagnóstico de Mastite e Residues de Antibióticos, 2020.

Mills, How to screen raw milk for hygiene quality at the dairy for bacteria and somatic cell count, Jan. 30, 2018.

IDEXX SNAP para deteccion especifica de residuos de contaminantes en leche, 2020.

Forcato, Milk Fat Content Measurement by a Simple UV Spectrophotometric Method: An Alternative Screening Method, American Dairy Science Association, Feb. 1, 2005.

Kucheryavskiy et al., Determination of fat and total protein content in milk using conventional digital imaging, Apr. 2014.

Zhu et al., A rapid method for measuring fat content in milk based on W-type optical fibre sensor system, Jul. 10, 2015.

Soyeurt et al., Mid-infrared prediction of bovine milk fatty acids across multiple breeds, production systems, and countries, American Dairy Science Association, Apr. 1, 2011.

Behkami et al., Classification of cow milk using artificial neural network developed from the spectral data of single-and three-detector spectrophotometers, Oct. 1, 2019.

International Searching Authority, PCT/IB2021/061582, dated Mar. 2, 2022.

* cited by examiner

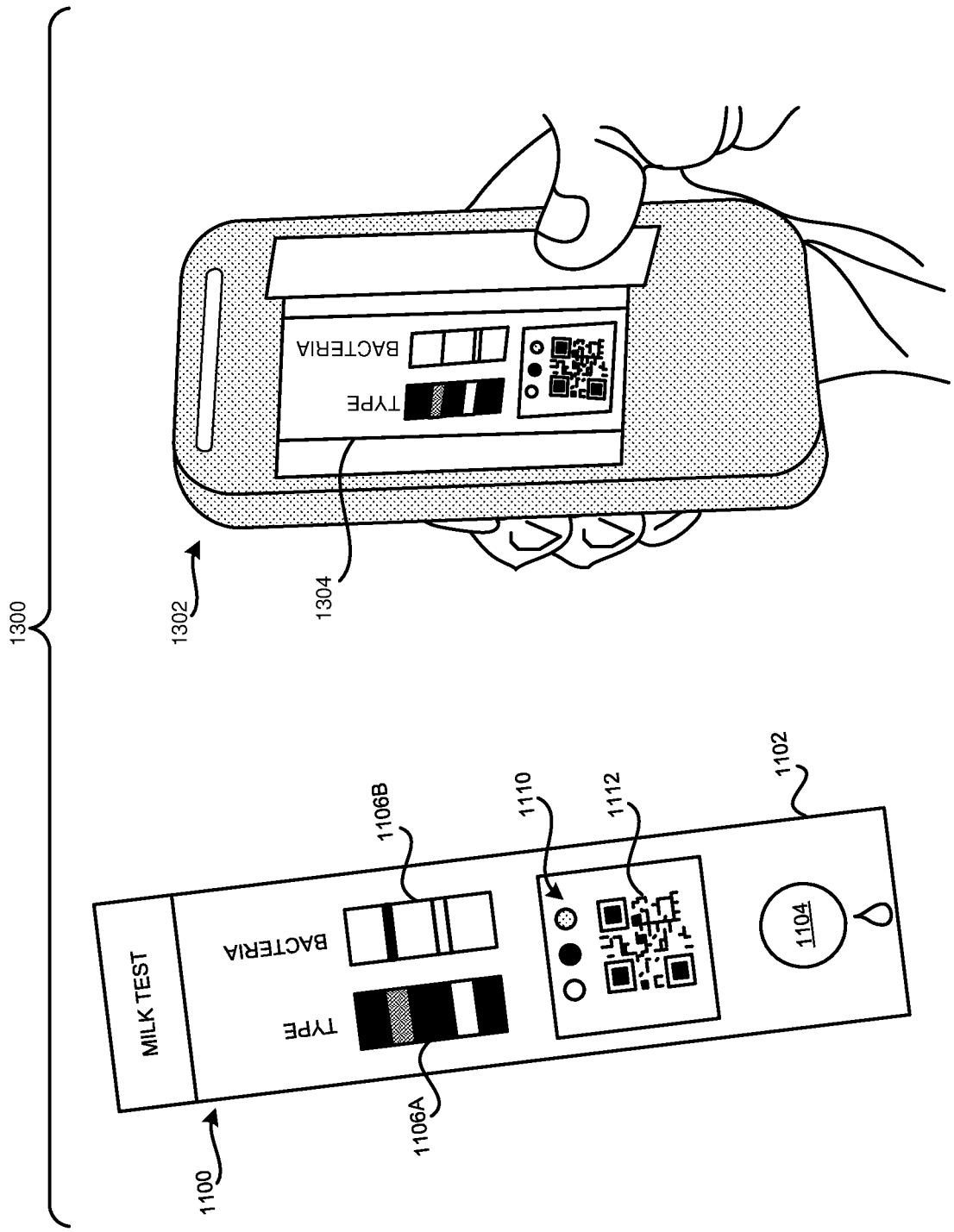

RAPID TEST DEVICE HAVING MULTIPLE HETEROGENEOUS DIAGNOSTIC METHODS

BACKGROUND

The present invention relates generally to a system and method for chemical and biochemical samples. More particularly, the present invention relates to a system and method for rapid test devices of chemical samples.

Portable diagnostic test devices, also known as Point of Care Testing (POCT) devices or rapid test devices, have been increasing in popularity in recent years. Commercially available rapid test devices have been introduced for a variety of healthcare applications, as well as other applications, such as veterinary testing, agricultural applications, environmental testing, and product quality evaluation.

Existing rapid test devices include lateral flow assays (LFAs) and colorimetric test strips. These two types of paper-based testing strips operate in different ways and have different requirements for sample volumes and deposition mechanisms.

LFAs are used for performing biological screening, such as detecting the presence of particular antibodies in test samples. A typical LFA is a handheld test device that has a sample pad for receiving a test sample. This deposited test sample flows through a series of different overlapped porous membranes. One of these membranes include regions having particles that react with the antibodies or antigens and other particles on the sample in certain result-indicating regions (e.g., test line and control line regions) to produce a color deposition that provides a visual indicator of test results.

Other existing test devices include colorimetric test strips used for chemical screening, such as detecting the presence of particular chemical compounds in test samples. Colorimetric test strips are paper-based chemical testing strips that typically need to be immersed in the test sample. The colorimetric test strip typically exhibits a ranged colorimetric response to a chemical reaction between a certain test sample compound and reagents embedded in paper fibers of the test strip. The resulting shade of color is typically one of several possible color outcomes that each correlate to respective concentrations of the target chemical element in the test sample.

SUMMARY

The illustrative embodiments provide for rapid test devices having multiple diagnostic methods. An embodiment includes a sample receiving region, a first diagnostic element that includes a colorimetric analysis region, and a second diagnostic element that includes a lateral flow assay analysis region. The embodiment also includes a first flow path that allows a first portion of a liquid deposited at the sample receiving region to flow to the first diagnostic element. The embodiment also includes a second flow path that allows a second portion of the liquid deposited at the sample receiving region to flow to the second diagnostic element.

An alternative embodiment includes a sample receiving region, a first diagnostic element that includes a colorimetric analysis region, and a second diagnostic element that includes a lateral flow assay analysis region. The embodiment also includes a first distribution substrate comprising a first hydrophilic region and a first hydrophobic region that defines a boundary of the first hydrophilic region, wherein the first hydrophilic region receives liquid deposited at the sample receiving region. The embodiment further includes a second distribution substrate comprising a second hydrophilic region that receives a first portion of liquid from the first hydrophilic region and allows the liquid to flow to the first diagnostic element, a third hydrophilic region that receives a second portion of liquid from the first hydrophilic region and allows the liquid to flow to the second diagnostic element, and a second hydrophobic region that opposes traversal of liquid from the second hydrophilic region to the third hydrophilic region.

An alternative embodiment includes a sample receiving region, a first diagnostic element that includes a colorimetric analysis region, and a second diagnostic element that includes a lateral flow assay analysis region. The embodiment also includes a first flow passageway comprising hydrophilic material between the sample receiving region and the first diagnostic element and a second flow passageway comprising hydrophilic material between the sample receiving region and the second diagnostic element. The embodiment further includes a flow barrier that repels liquid between a portion of the first flow passageway and the second flow passageway.

An alternative embodiment includes a sample receiving region, a first diagnostic element that includes a colorimetric analysis region, and a second diagnostic element that includes a lateral flow assay analysis region. The embodiment also includes a multiplex flow path that receives liquid deposited at the sample receiving region, allows a first portion of the liquid to flow to the first diagnostic element, and allows a second portion of the liquid to flow to the second diagnostic element.

An alternative embodiment includes a sample receiving region, a first diagnostic element that includes a colorimetric analysis region, and a second diagnostic element that includes a lateral flow assay analysis region. The embodiment also includes a hydrophobic structure that defines a first flow path from the sample receiving region to the first diagnostic element and defines a second flow path from the sample receiving region to the second diagnostic element.

Any of these embodiments may further comprise a housing, where the sample receiving region comprises a first opening defined by the housing. Some such embodiments further comprise a graphical element on the housing, where the graphical element is encoded with information associated with the first diagnostic element and the second diagnostic element.

In any of these embodiments, the first diagnostic element comprises a sample conveying portion that guides the first portion of the liquid to a colorimetric reacting region. In some such embodiments, the colorimetric analysis region comprises a first colorimetric reaction area, a second colorimetric reaction area, and a hydrophobic area that are at least partially disposed between the first colorimetric reaction area and the second colorimetric reaction area.

Any of these embodiments may further comprise a pressure point element that urges a first membrane of the second diagnostic element towards a second membrane of the second diagnostic element.

Various embodiments advantageously provide multiple different diagnostic methods that effectively provide respective different test results from a single test sample. Various embodiments advantageously allow for the flow of the sample to each of the multiple different diagnostic methods, allowing multiple tests to be performed using a single test sample.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

FIG. 13 depicts a mobile application used with a multiplexed rapid test device in accordance with an illustrative embodiment.

DETAILED DESCRIPTION

Figure 1:
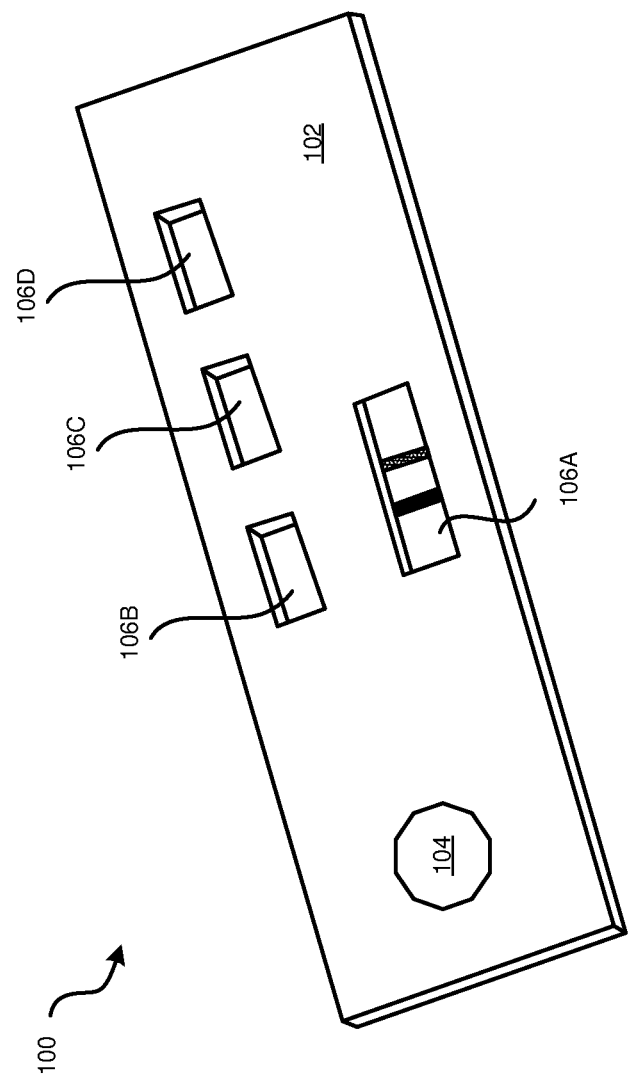
FIG. 1 depicts a plan view of a multiplexed rapid test device according to an embodiment of the present invention.

A wide variety of rapid test devices have been developed in recent years that can quickly provide test results outside of a lab environment and without the need for lab equipment. Two main types of such devices are lateral flow assays (LFAs) and colorimetric test strips. Both LFAs and colorimetric test strips use a paper-based diagnostic substrate, LFAs differ from colorimetric test strips in several ways, including many different operation principles. For example, LFAs and colorimetric test strips need different amounts of sample, apply different means to enable contact with reagents, require different reaction times and results may be displayed in different formats.

A desirable characteristic of a rapid test device is the ability to execute various tests in a single rapid test device with a single test sample. The ability to perform multiple tests from a single test sample saves time and money, and it reduces ambiguity caused by sample conditions that change over time while various different test devices are employed for different types of tests. Performing multiple tests from a single test sample also reduces the complexity of planning, performing, and evaluating the results of multiple tests using separate test devices to perform different types of tests. For example, different test devices require different testing techniques, which can inadvertently be interchanged or confused due to human error.

Some of the tests, for instance, serologic ones, employ LFAs to detect the presence or absence of a target antibody. Other tests employ colorimetric reacting indicators on a paper strip or dipstick (e.g., colorimetric test strips) to evaluate the concentration of a certain chemical element in a test sample. Many situations arise in which it is desired to test a particular sample for the presence or absence of a target antibody and also evaluate the concentration of some chemical element in the same test sample.

Despite the desirability of performing multiple tests from a single test sample, fundamental differences between LFAs and colorimetric test strips have prevented the integration of these different types of tests into a single test device. For example, colorimetric test strips typically require immersion in a liquid test sample for some specified period of time to guarantee sufficient contact with the test sample. However, the amount of liquid used by the colorimetric test strip is problematic for an LFA. The amount of liquid applied to an LFA is limited through the use of a wicking pad that prevents backflow of excess liquid from a test droplet over the test reaction area. Otherwise, the excess liquid will reduce the sensitivity of the LFA reaction area. Complete immersion of an LFA with a colorimetric test strip would overwhelm the wicking pad and render the LFA test results inconclusive.

The present embodiments recognize that, integration of LFA and colorimetric test strip types of tests into a test device that performs both types of tests from a single test sample is possible despite the challenges that have prevented such integration in the past. The illustrative embodiments address and solve this technical problem by introducing an asymmetrical sample distribution capability in a rapid test device that results in disproportionate amounts of a single test sample being distributed to different diagnostic elements of the test device. Advantageously, the asymmetrical sample distribution allows a relatively greater amount of the sample to flow to a diagnostic element that benefits from exposure to a greater amount of the test sample and allows a relatively smaller amount of the sample to flow to another diagnostic element that would be damaged or hindered by exposure to too much of the test sample. For example, an embodiment of a rapid test device has a colorimetric type of diagnostic element and an LFA type of diagnostic element and allows a disproportionately greater amount of a single test sample to flow to the colorimetric type of diagnostic element and a disproportionately lesser amount of the single test sample to flow to the LFA type of diagnostic element, thereby allowing the colorimetric type of diagnostic element to receive an adequate amount of liquid for generating a test result without overwhelming the LFA type of diagnostic element, which is therefore also able to generate a test result from the lesser, but more appropriate amount of the test sample.

The term "sample" or "test sample" herein means a volume of a liquid, solution, or suspension, intended to be subjected to qualitative or quantitative determination of any of its properties, such as the presence or absence of a component, the concentration of a component, etc. Typical samples in the context of the present embodiments as described herein are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. Still other types of samples are liquids of any kind, for example water for water analysis or tap water quality testing, industrial and environmental testing, pool and spa testing, lake and stream testing, aquarium testing, food safety monitoring, and environmental pollution detection. Simple, quick and accurate testing is advantageous, and a test strip must have the necessary detection capability. Thus, the disclosed embodiments are equally applicable to bodily and non-bodily samples.

The term "lateral flow assay" as discussed herein refers to any device that receives fluid, such as a chemical or biochemical sample, and includes a laterally disposed fluid transport or flow path along which specific areas will provide various features like reagents, and filters, through which sample traverses under the influence of capillary or other applied forces.

The terms "region" and "area" are used in the context of this description, examples and claims to define parts of the fluid flow path on a substrate.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

In some embodiments, a rapid test device comprises a sample receiving region, a first diagnostic element that includes a colorimetric analysis region, and a second diagnostic element that includes a lateral flow assay analysis region. In some such embodiments, an asymmetrical sample distribution is provided by first and second flow paths, where the first flow path that allows a first portion of a liquid deposited at the sample receiving region to flow to the first diagnostic element and the second flow path allows a second portion of the liquid deposited at the sample receiving region to flow to the second diagnostic element.

In some embodiments, an asymmetrical sample distribution is provided by first and second distribution substrates. In such embodiments, the first distribution substrate includes a first hydrophilic region that receives liquid deposited at the sample receiving region. The first distribution substrate also includes a first hydrophobic region that defines a boundary of the first hydrophilic region. The second distribution substrate includes a second and third hydrophilic regions that each receive respective portions of liquid from the first hydrophilic region. The second hydrophilic region allows liquid to flow to the first diagnostic element, while the third hydrophilic region allows liquid to flow to the second diagnostic element. The second distribution substrate also includes a second hydrophobic region that opposes traversal of liquid from the second hydrophilic region to the third hydrophilic region and vice-versa. In some embodiments, the second hydrophobic region allows for controlling the respective sizes of the second and third hydrophilic regions according to the desired proportion of liquid sought to be delivered to each of the diagnostic elements.

In some embodiments, an asymmetrical sample distribution is provided by a first flow passageway comprising hydrophilic material between the sample receiving region and the first diagnostic element and a second flow passageway comprising hydrophilic material between the sample receiving region and the second diagnostic element. In some such embodiments, a flow barrier that repels liquid is provided between a portion of the first flow passageway and the second flow passageway. In some such embodiments, the flow barrier allows for controlling the respective sizes of the second and third hydrophilic regions according to the desired proportion of liquid sought to be delivered to each of the diagnostic elements.

In some embodiments, an asymmetrical sample distribution is provided by a multiplex flow path that receives liquid deposited at the sample receiving region, allows a first portion of the liquid to flow to the first diagnostic element, and allows a second portion of the liquid to flow to the second diagnostic element. In some such embodiments, the multiplex flow path allows for controlling the respective portions of liquid that flow to the diagnostic elements according to the desired proportion of liquid sought to be delivered to each of the diagnostic elements.

Also, in some embodiments, an asymmetrical sample distribution is provided by a hydrophobic structure that defines a first flow path from the sample receiving region to the first diagnostic element and defines a second flow path from the sample receiving region to the second diagnostic element. In some such embodiments, the hydrophobic structure allows for controlling the respective sizes of the first and second flow paths according to the desired proportion of liquid sought to be delivered to each of the diagnostic elements.

With reference to FIG. 1, this figure depicts a plan view of a multiplexed rapid test device 100 in accordance with an illustrative embodiment. A top cover 102 has openings (e.g., windows) for a sample deposition to perform a test, and to display the test results. For example, the top cover 102 has a sample receiving region 104 arranged over a reservoir that retains the sample. The top cover 102 also has a plurality of test result windows 106A-106D that show the results of respective tests. While the illustrated embodiment includes a sample receiving region 104 that is circular, embodiments are not limited to any particular shape. For example, the sample receiving region can be square, rectangular, triangular, oblong, irregularly shaped, etc. Similarly, the illustrated embodiment includes four test results in windows 106A-106D because this multiplexed rapid test device includes four diagnostic regions. However, there can be larger or smaller quantities of diagnostic regions, and there may be a test result window 106 for each diagnostic region. Alternatively, there may be a single test result window sufficiently large to display the test results of multiple diagnostic regions.

Figure 2:
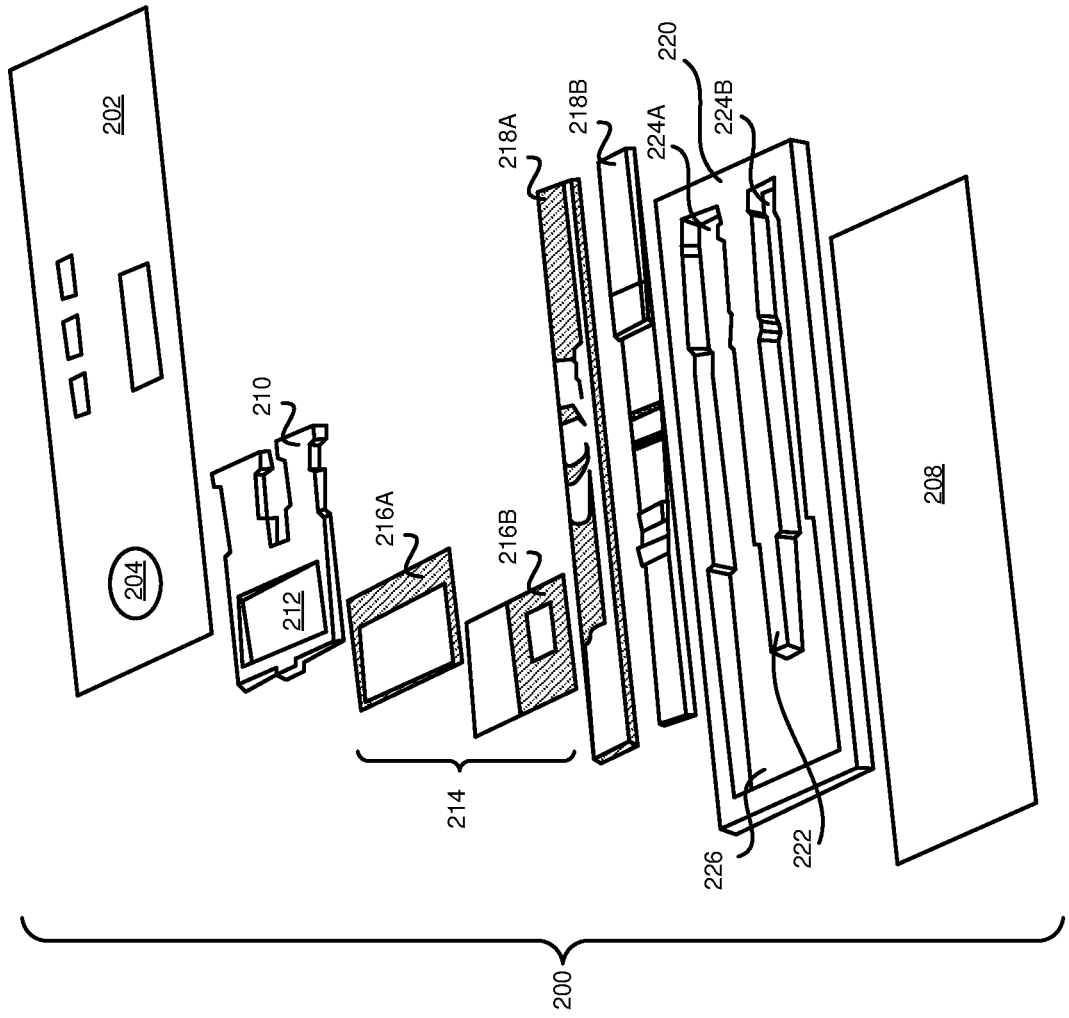
FIG. 2 depicts an exploded view of a multiplexed rapid test device according to an embodiment of the present invention.

With reference to FIG. 2, this figure depicts an exploded view of a multiplexed rapid test device 200 in accordance with an illustrative embodiment. In a particular embodiment, multiplexed rapid test device 200 is an example of multiplexed rapid test device 100 of FIG. 1.

In the illustrated embodiment, the multiplexed rapid test device 200 has a top cover 202 and bottom cover 208 attached to opposing sides of a spacer element 220 such that the top cover 202, bottom cover 208, and spacer element 220 collectively constitute an example of a housing. In some embodiments, the top cover 202, bottom cover 208, and spacer element 220 are formed of an impermeable material, for example paper that has a hydrophobic coating so as to be impermeable to the test sample and buffer solution. In some embodiments, the top cover 202, bottom cover 208, and spacer element 220 all formed of impermeable material collectively constitute an example of an impermeable housing.

In the illustrated embodiment, the multiplexed rapid test device 200 has an internal pressure point element 210 that has a body with an upper surface, a lower surface, and an opening in the body that defines an internal reservoir 212 that receives a test sample deposited at the sample receiving region 204. In addition, the internal reservoir 212 is configured to receive an expected sample volume of liquid at once, (e.g., a predetermined volume of ul) and to retain the sample volume for a period while the liquid is being wicked into a fluid distribution assembly 214. By integrating the internal reservoir 212 within the rapid test device 200, there is a reduction/elimination of overflow of the sample onto the outside the top cover 202 and bottom cover 208. In addition, the integration of the internal reservoir 212 reduces/eliminates sample loss due to spillage.

With continued reference to the illustrative embodiment of FIG. 2, the fluid distribution assembly 214 is arranged in fluid communication with a lower surface of the internal reservoir 212. The fluid distribution assembly 214 comprises a plurality of distribution substrates 216A-216B that collectively divide a portion of a test sample deposited in the internal reservoir 212 among a plurality of flow paths. In turn, the flow paths are in fluid communication of the flow lines of each of a plurality of diagnostic elements 218A and 218B. While the illustrated embodiment of the fluid distribution assembly 214 includes two distribution substrates 216A-216B, alternative embodiments of the fluid distribution assembly 214 include larger or smaller quantities of distribution substrates. Also, while the illustrated embodiment of the multiplexed rapid test device 200 includes two diagnostic elements 218A and 218B, alternative embodiments of the multiplexed rapid test device 200 include larger or smaller quantities of diagnostic elements.

In the illustrated embodiment, the distribution substrates 216A and 216B each has respective wax-defined hydrophilic channels fabricated in the same sample pad material of the diagnostic elements 218A and 218B to enhance sample distribution into the diagnostic elements 218A and 218B. By using the same material for the distribution substrates 216A and 216B as the diagnostic elements 218A and 218B, a more effective transfer of fluid from the distribution substrates 216A, 216B to the diagnostic elements 218A, 218B is achieved. Also, by using carefully designed wax-defined channels, the amount of test sample retained by the fluid distribution assembly 214 decreases. In addition, the design of the wax-defined channels achieves a desired distribution under varying conditions (e.g., the multiplexed rapid test device 200 being tilted, dropped, etc.).

In the illustrated embodiment, the multiplexed rapid test device 200 includes spacer element 220 as an intermediate support layer. As shown in the illustrative embodiment of FIG. 2, the spacer element 220 is constructed of a material that is pre-treated (e.g., coated) to make the material impermeable to the liquid sample and a buffer solution. The material used to construct the spacer element 220 in this embodiment is cardboard, but the construction is not limited to this material. For example, chipboard may be used.

In the illustrated embodiment, the spacer element 220 includes at least one partitioning strip 222 arranged to separate the diagnostic elements 218A and 218B, that are housed in respective areas 224A, 224B defined by the spacer element 220 so as to prevent cross contamination. The partitioning strip 222, along with the rest of the spacer element 220, can also serve to ensure that there is a gap between the top cover 202 and the diagnostic elements 218A and 218B to prevent contamination of the flow lines, or impedance of the flow lines, by the top cover 202 inadvertently coming into contact with the surface of the diagnostic elements 218A and 218B. In some embodiments, the spacer element 220 may include more than one partitioning strip 222 if the quantity of the diagnostic elements 218A and 218B exceeds two. For example, an alternative embodiment includes three diagnostic elements 218 and two partitioning strips 222 where the two partitioning strips 222 separate the three diagnostic elements 218, and another alternative embodiment includes n diagnostic elements 218 and n−1 partitioning strips 222 where the n−1 partitioning strips 222 separate the n diagnostic elements 218, where n is any desired integer. By permitting the use of multiple diagnostic elements 218 that are housed in the spacer element 220, tests for multiple reagents may be performed from a single deposition sample. It is also shown in this embodiment that the partitioning strip 222 does not partition the entire area defined by the spacer element 220. There is an un-partitioned area 226 for the arrangement of the fluid distribution assembly 214 and the internal reservoir 212. The impermeable bottom cover 208 and the spacer element 220 combine to form a housing element (in conjunction with the top cover 202) for the arrangement and alignment of the internal reservoir 212, the fluid distribution assembly 214 and the two or more diagnostic elements 218.

In the illustrated embodiment, the internal pressure point element 210 is arranged to enhance contact reliability at interfaces between the fluid distribution assembly 214 and the diagnostic elements 218A and 218B.

Figure 3:
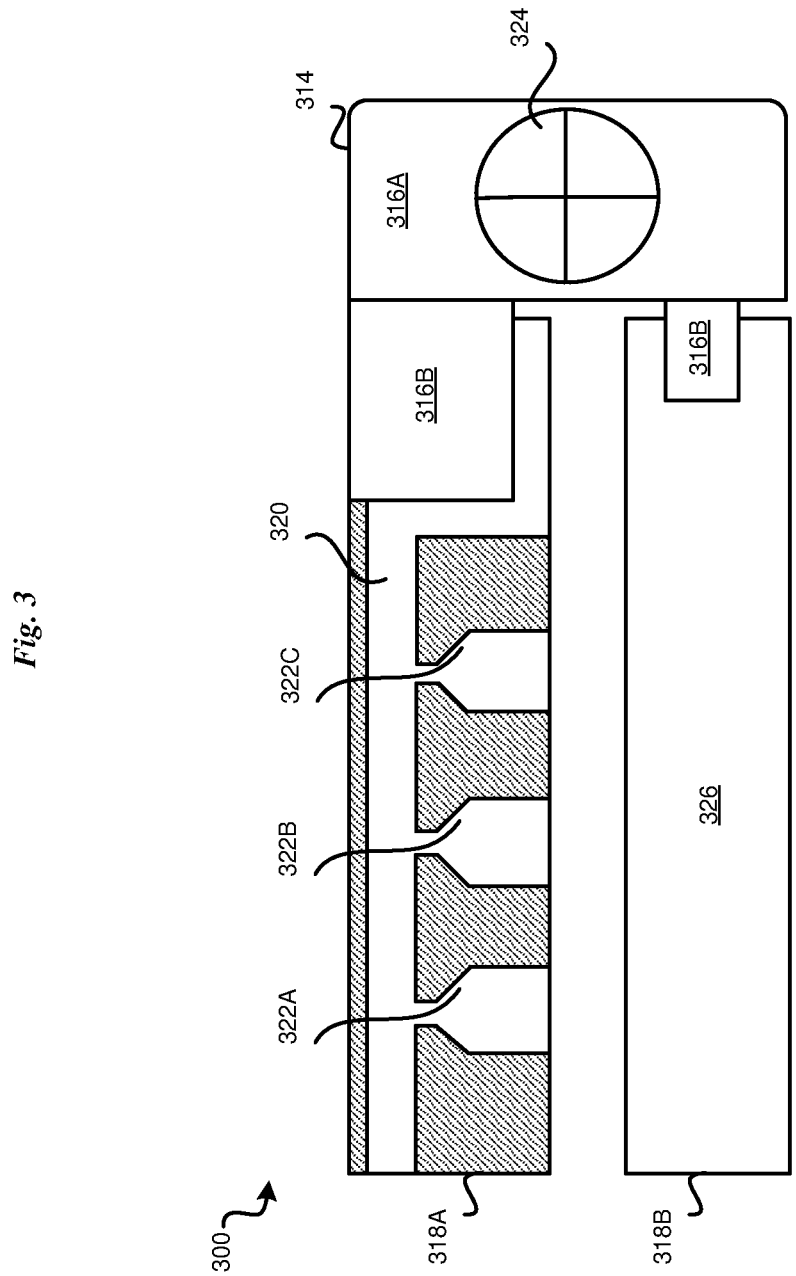
FIG. 3 depicts a plan view of a flow path representation of a multiplexed rapid test device in accordance with an illustrative embodiment.

With reference to FIG. 3, this figure depicts a plan view of a flow path representation 300 of a multiplexed rapid test device in accordance with an illustrative embodiment. The flow path representation 300 is an example of a flow path highlighting the hydrophilic areas of multiplexed rapid test device 100 of FIG. 1 or multiplexed rapid test device 200 of FIG. 2.

In the illustrated embodiment, the flow path representation 300 includes diagnostic elements 318A and 318B, which are examples of diagnostic elements 218A and 218B, respectively, of FIG. 2. The flow path representation 300 also includes fluid distribution assembly 314 comprising distribution substrates 316A and 316B, where fluid distribution assembly 314 is an example of fluid distribution assembly 214 and distribution substrates 316A and 316B are examples of 216A and 216B, respectively, of FIG. 2. In the representation shown in FIG. 3, hydrophobic portions of distribution substrates 316A and 316B are not shown for clarity purposes.

In the flow path representation 300, the diagnostic element 318A is a representation of a colorimetric type of diagnostic element, and the diagnostic element 318B is a representation of a lateral flow assay type of diagnostic element. The diagnostic element 318A includes hydrophilic channel 320 and a plurality of colorimetric reagent areas 322A-322C defined by hydrophobic regions 328 (shown with shading). Also, in the illustrated embodiment, the diagnostic element 318B includes a hydrophilic material 326. Typically, the flow of liquid from a test sample 324 is from the distribution substrate 316A, through the distribution substrate 316B, toward the hydrophilic channel 320 and hydrophilic material 326, and for the diagnostic element 318A, from the hydrophilic channel 320 into each of the colorimetric reagent areas 322A-322C. In the flow path representation 300, the hydrophilic channel 320, colorimetric reagent areas 322A-322C, and 326 comprise a porous medium, such as paper, and the liquid is pulled by the wicking effect of the porous medium without the need for external pumps.

Figure 4:
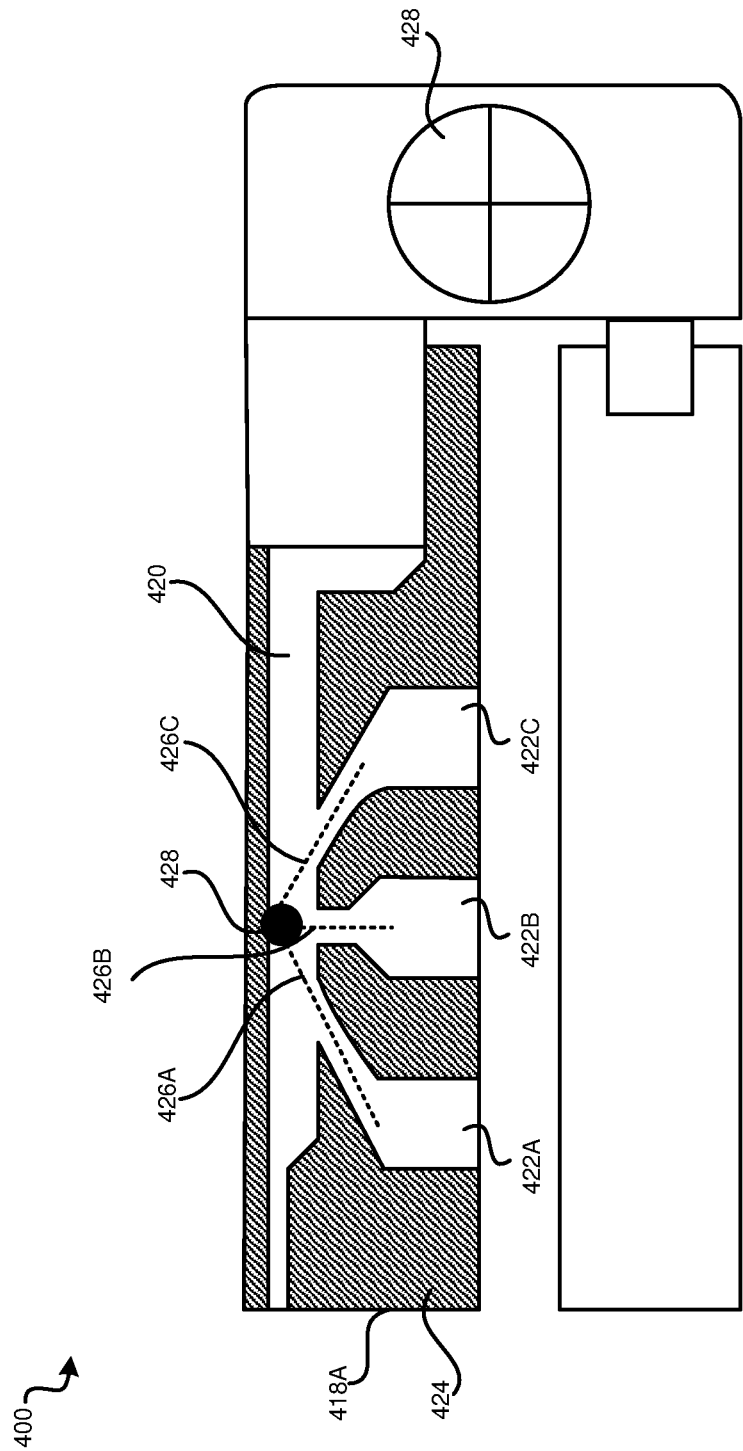
FIG. 4 depicts a plan view of a flow path representation of a multiplexed rapid test device in accordance with an illustrative embodiment.

With reference to FIG. 4, this figure depicts a plan view of a flow path representation 400 of a multiplexed rapid test device in accordance with an illustrative embodiment. In a particular embodiment, the flow path representation 400 is substantially the same as the flow path representation 300 of FIG. 3 except as described.

In the illustrated embodiment, the flow path representation 400 includes an alternative embodiment of a colorimetric type of diagnostic element 418A. The diagnostic element 418A includes hydrophilic channel 420 and a plurality of colorimetric reagent areas 422A-422C defined by hydrophobic regions 424. Also, the diagnostic element 418A further includes hydrophilic sub-channels 426A-426C that extend towards a common point 428 as illustrated by broken lines extending through the sub-channels 426A-426C to the common point 428. Compared to the representation shown in FIG. 3, the sub-channels 426A-426C is an example of a flow path design to allow the liquid from a test sample 430 to reach the colorimetric reagent areas 422A-422C more quickly.

Figure 5:
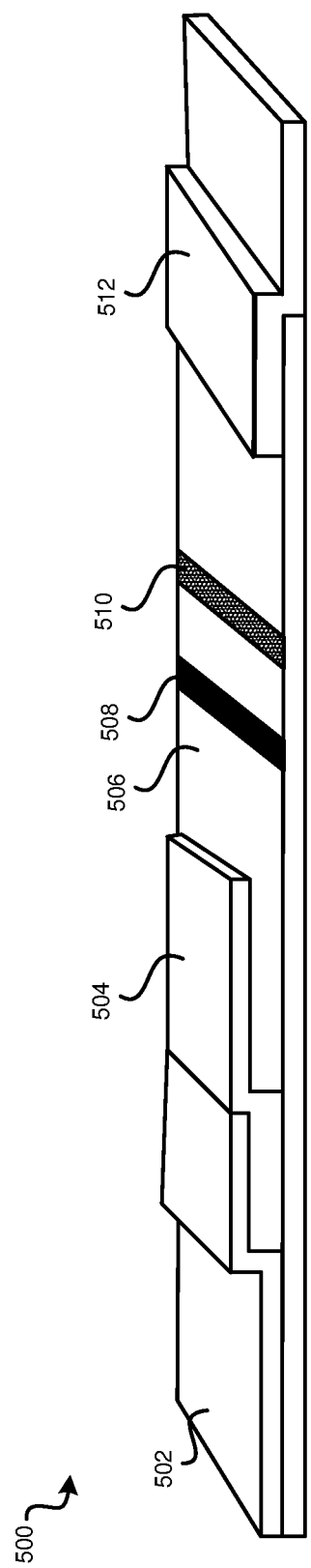
FIG. 5 depicts a perspective view of a lateral flow assay in accordance with an illustrative embodiment.

With reference to FIG. 5, this figure depicts a perspective view of a lateral flow assay 500 in accordance with an illustrative embodiment. In a particular embodiment, the lateral flow assay 500 is an example of the lateral flow assay type of diagnostic element 318B of FIG. 3.

In the illustrated embodiment, the lateral flow assay 500 includes a sample pad/blood separator 502, a conjugate pad 504, a membrane 506 with a test line 508 and a control line 510, and a wicking pad 512. Typically, the sample pad 502, the conjugate pad 504, the membrane 506, and the wicking pad 512 comprise a porous medium, such as paper. In such embodiments, liquid flows from the sample pad 502 toward the wicking pad 512, and the liquid is pulled by the wicking effect of the porous medium without the need for external pumps.

Figure 6:
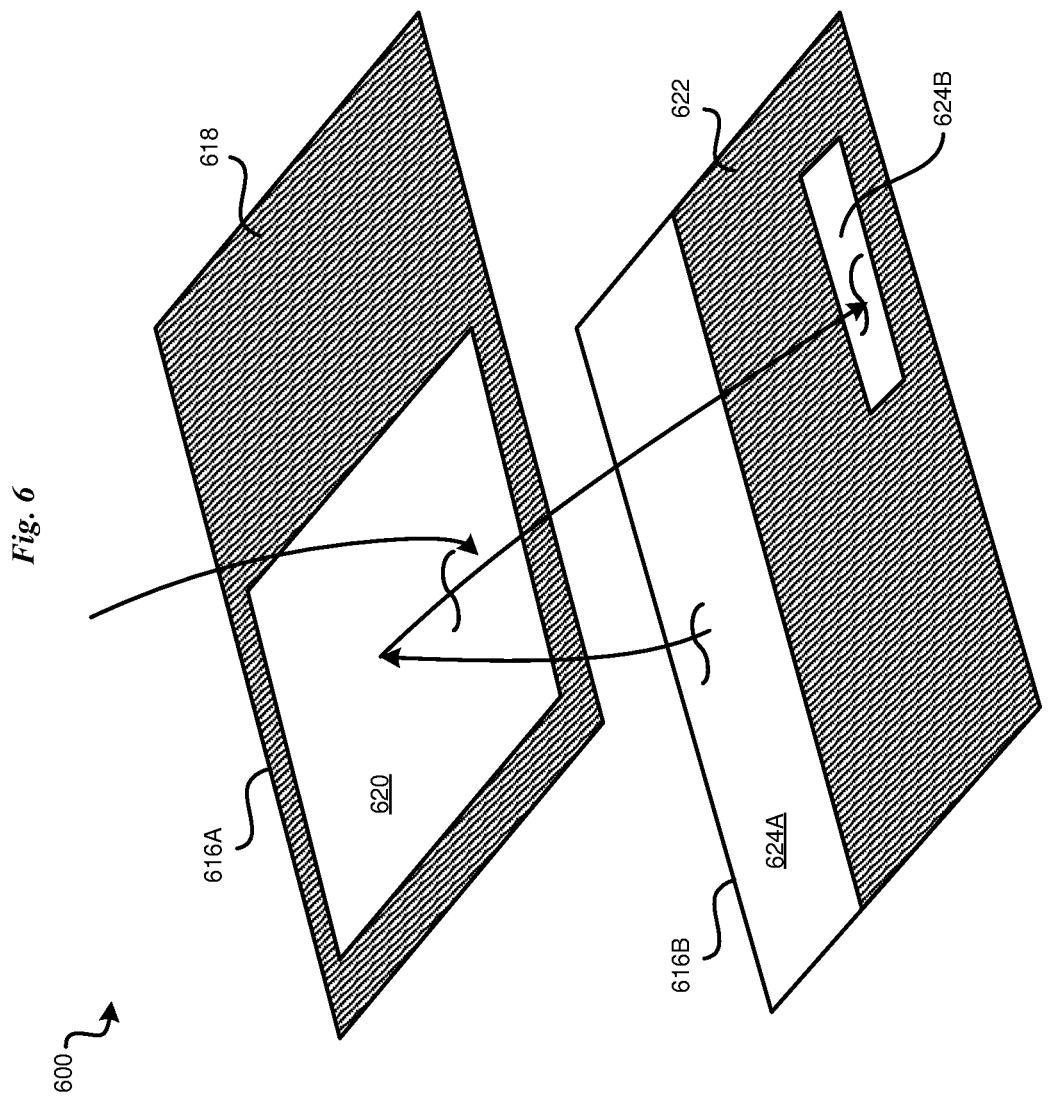
FIG. 6 depicts an exploded view of a fluid distribution assembly in accordance with an illustrative embodiment.

With reference to FIG. 6, this figure depicts an exploded view of a fluid distribution assembly 600 in accordance with an illustrative embodiment. In a particular embodiment, the fluid distribution assembly 600 is an example of the fluid distribution assembly 214 of FIG. 2.

In the illustrated embodiment, the fluid distribution assembly 600 comprises a plurality of distribution substrates 616A and 616B that collectively divide a portion of a test sample deposited in the internal reservoir (e.g., internal reservoir 212 of FIG. 2) among a plurality of flow paths. In turn, the flow paths are in fluid communication of the flow lines of each of a plurality of diagnostic elements (e.g., diagnostic elements 218A and 218B of FIG. 2). While the illustrated embodiment of the fluid distribution assembly 214 includes two distribution substrates 616A and 616B, alternative embodiments of the fluid distribution assembly 600 include larger or smaller quantities of distribution substrates.

The fluid distribution assembly 600 is a multi-layer assembly arranged in fluid communication with the internal reservoir and diagnostic elements. The multi-layer fluid distribution assembly 600 includes distribution substrate 616A as a top layer and distribution substrate 616B as a lower layer. The distribution substrate 616A comprises a hydrophobic wax-filled area 618, and a hydrophilic paper channel 620. The hydrophilic paper channel 620 is in fluid communication with a plurality of flow paths configured to distribute at least a portion of a test sample deposited in an internal reservoir to multiple diagnostic elements in a ratio that satisfies the liquid volume requirements of the various diagnostic elements. For example, in some embodiments, the amount of liquid from the test sample that is needed by a diagnostic element may vary depending on whether the diagnostic element is a colorimetric type of diagnostic element or a lateral flow assay type of diagnostic element.

In the illustrated embodiment, the distribution substrate 616B comprises a hydrophobic wax-filled area 622, and a plurality of hydrophilic paper channels 624A and 624B. The hydrophilic paper channels 624A and 624B are both in fluid communication with the hydrophilic paper channel 620 of the distribution substrate 616A. In addition, the hydrophilic paper channel 624A is in fluid communication with a first diagnostic element and the hydrophilic paper channel 624B is in fluid communication with a second diagnostic element. The amount of liquid from a test sample that flows to a diagnostic element depends on the area of the hydrophilic paper channels between the internal reservoir and the respective diagnostic element. Thus, the hydrophilic paper channel 624A is much larger than the hydrophilic paper channel 624B to allow more liquid to flow to a diagnostic element that is in fluid communication with the hydrophilic paper channel 624A than would flow to a diagnostic element that is in fluid communication with the hydrophilic paper channel 624B. Thus, the plurality of flow paths are configured to distribute at a portion of a test sample deposited in an internal reservoir to multiple diagnostic elements in a ratio that satisfies the liquid volume requirements of the various diagnostic elements.

In some embodiments, the sizes of the hydrophilic paper channels of the respective distribution substrate 616 are controlled based on various constructions of wax patterns of the distribution substrates consistent with illustrative embodiments of the present disclosure. In the illustrated embodiment, the distribution substrate 616A has a wax pattern that is different than the wax pattern of the distribution substrate 616B. In some embodiments, the wax patterns are deposited on the paper sheet top and/or bottom surfaces by means of a wax printer or other known methods to define the channel design prior to undergoing a reflow process. In some embodiments, the reflow process includes applying heat to melt the wax and impregnate the thickness of the paper sheet to create hydrophobic barriers to the movement of fluid. Depending on the paper sheet thickness, gray scale wax features are used to partially penetrate the thickness of the paper and can be used to create three-dimensional wax barriers, that is, on the plane and through the thickness of the paper. In some embodiments, a grey scale wax feature maintains hydrophobicity after reflowing.

Figure 7:
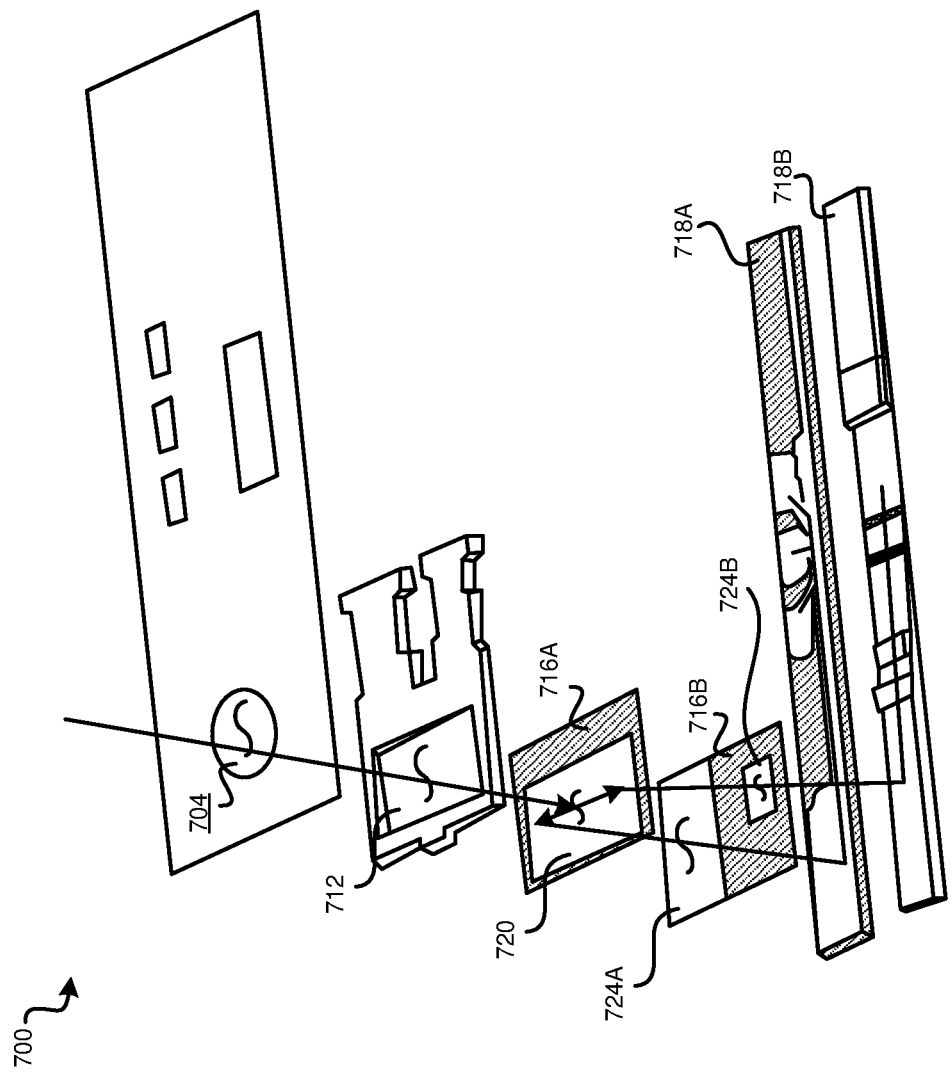
FIG. 7 depicts an exploded view of a multiplexed rapid test device in accordance with an illustrative embodiment.

With reference to FIG. 7, this figure depicts an exploded view of a multiplexed rapid test device 700 in accordance with an illustrative embodiment. In a particular embodiment, multiplexed rapid test device 700 is an example of multiplexed rapid test device 200 of FIG. 2.

In the illustrated embodiment, the multiplexed rapid test device 700 may be substantially the same as multiplexed rapid test device 200 shown in FIG. 2. The view in FIG. 7 includes flow lines indicating the location and direction of flow paths from a sample receiving region 704 to an internal reservoir 712, then to hydrophilic paper channel 720 of the distribution substrate 716A, and then is split between the hydrophilic paper channels 724A and 724B of the distribution substrate 716B, which allow flow of the liquid to the diagnostic elements 718A and 718B, respectively.

Figure 8:
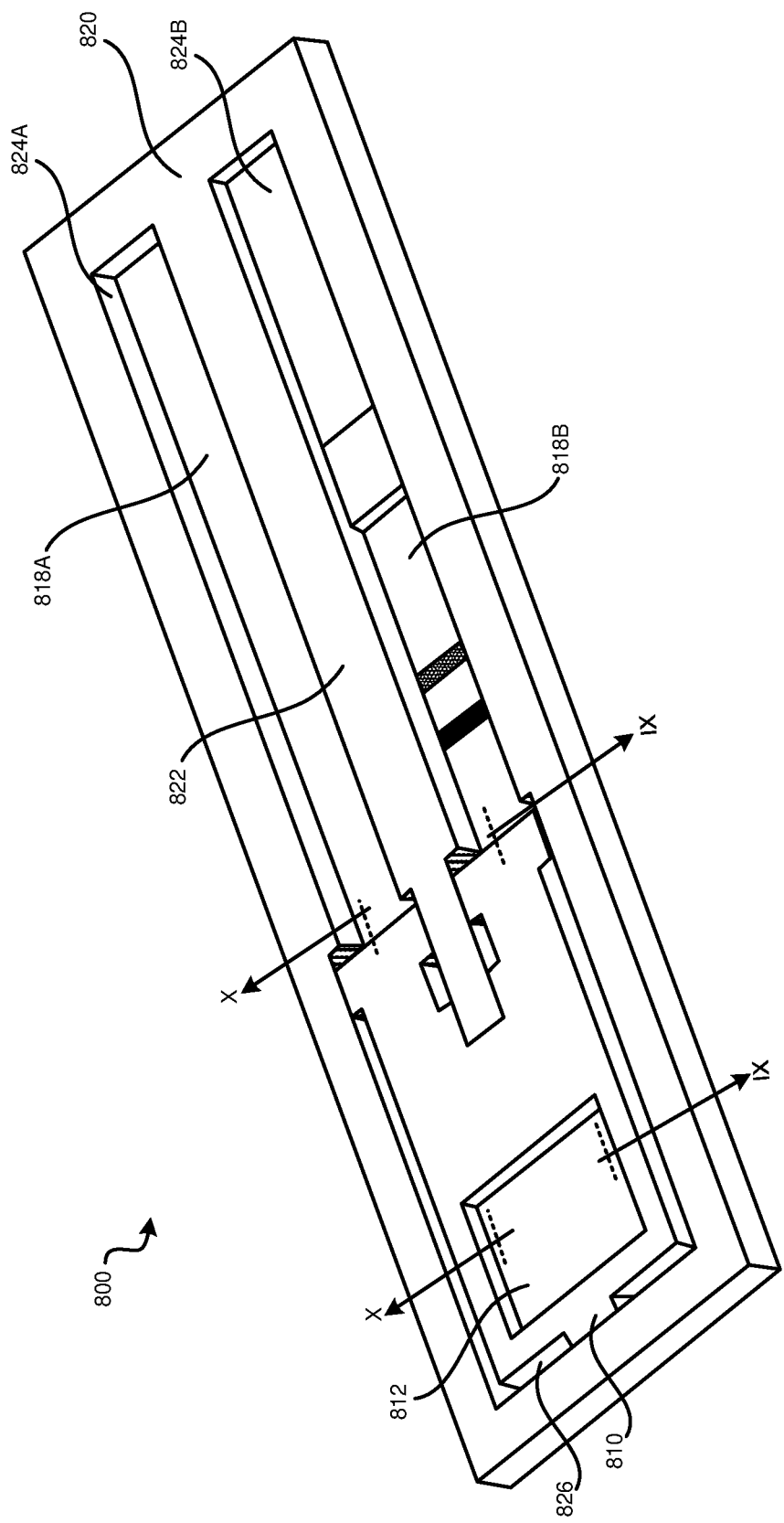
FIG. 8 depicts a perspective view of a multiplexed rapid test device in accordance with an illustrative embodiment.

With reference to FIG. 8, this figure depicts a perspective view of a multiplexed rapid test device 800 in accordance with an illustrative embodiment. In the view shown in FIG. 8, the top cover is not shown in order to more clearly describe the internal assembly of the test device 800. In a particular embodiment, multiplexed rapid test device 800 is an example of multiplexed rapid test device 200 of FIG. 2.

The multiplexed rapid test device 800 may be substantially the same as multiplexed rapid test device 200 shown in FIG. 2. The view in FIG. 8 shows the assembled components without the top cover (e.g., top cover 202 of FIG. 2). The multiplexed rapid test device 800 includes a spacer element 820 as an intermediate support layer. As shown in the illustrative embodiment of FIG. 8, the spacer element 820 includes at least one partitioning strip 822 arranged to separate the diagnostic elements 818A and 818B that are housed in respective areas 824A, 824B defined by the spacer element 820 so as to prevent cross contamination. The partitioning strip 822, along with the rest of the spacer element 820, can also serve to ensure that there is a gap between the top cover (e.g., top cover 202 of FIG. 2) and the diagnostic elements 818A and 818B to prevent contamination of the flow lines, or impedance of the flow lines, by the top cover inadvertently coming into contact with the surface of the diagnostic elements 818A and 818B.

In some embodiments, the spacer element 820 may include more than one partitioning strip 822 if the quantity of the diagnostic elements 818A and 818B exceeds two. For example, an alternative embodiment includes three diagnostic elements 818 and two partitioning strips 822 where the two partitioning strips 822 separate the three diagnostic elements 818, and another alternative embodiment includes n diagnostic elements 818 and n−1 partitioning strips 822 where the n−1 partitioning strips 822 separate the n diagnostic elements 818, where n is any desired integer. By permitting the use of multiple diagnostic elements 818 that are housed in the spacer element 820, tests for multiple reagents may be performed from a single deposition sample. It is also shown in this embodiment that the partitioning strip 822 does not partition the entire area defined by the spacer element 820. There is an un-partitioned area 826 for the arrangement of the fluid distribution assembly 214 and the internal reservoir 812. The internal pressure point element 810 is nested in the un-partitioned area 826 defined by the spacer element 820 and arranged to enhance contact reliability at interfaces of the diagnostic elements 818A and 818B.

Figure 9:
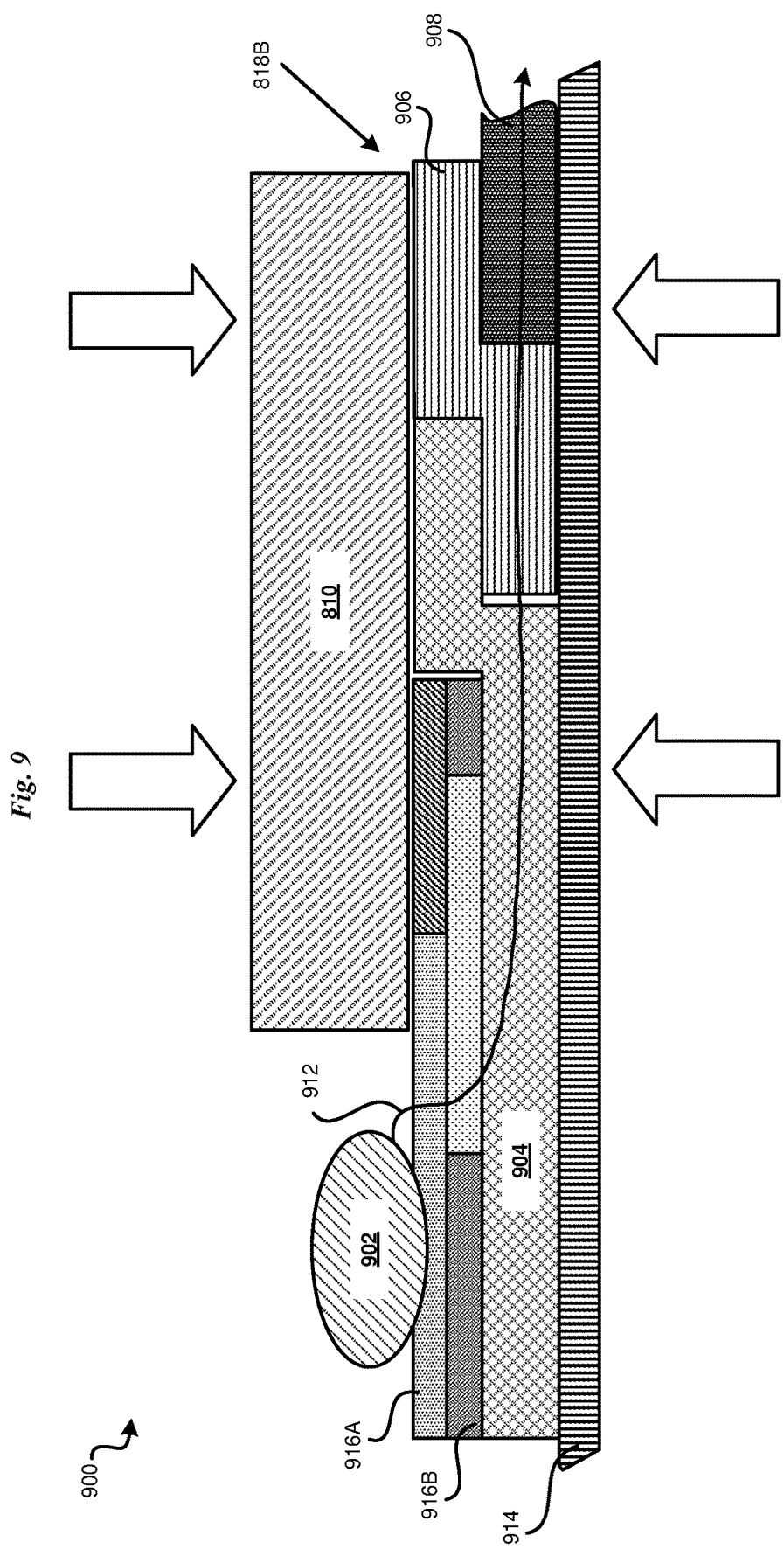
FIG. 9 depicts a cross-sectional view taken along section lines IX-IX of FIG. 8 in accordance with an illustrative embodiment.

With reference to FIG. 9, this figure depicts a cross-sectional view 900 taken along section lines IX-IX of FIG. 8 in accordance with an illustrative embodiment. In the illustrated embodiment, the block arrows indicate directions of force applied to inner layers by the internal pressure point element 810 and the bottom cover 914. The internal pressure point element 810 is arranged to enhance contact reliability at interfaces of the diagnostic element 818B and distribution substrates 916A and 916B along the flow path 912 taken by liquid of a test sample 902. The test sample 902 travels through hydrophilic regions of the distribution substrates 916A and 916B to lateral flow assay type diagnostic element 818B, specifically to the sample pad 904, then to the conjugate pad 906, and then to the membrane 908. Thus, it keeps the interfaces between these various components urged together to force the liquid to travel through the various components rather than leak out over or between layers.

Figure 10:
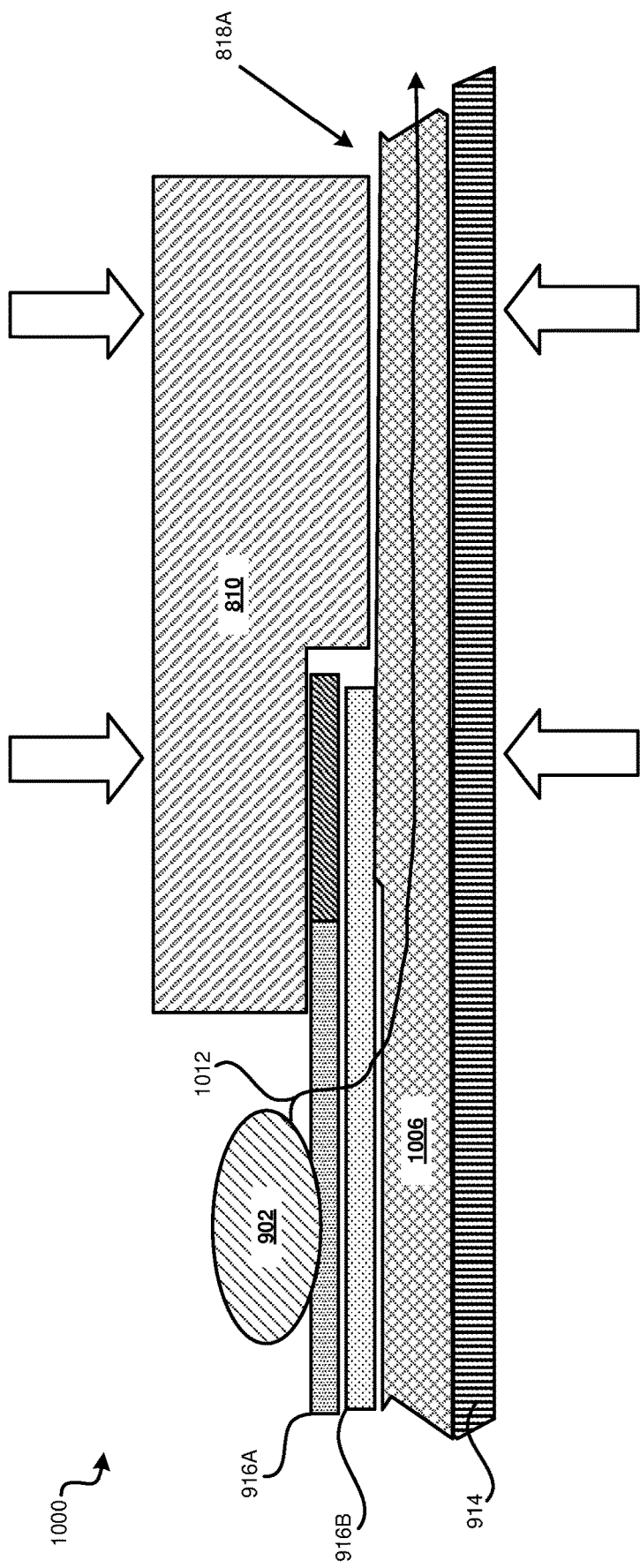
FIG. 10 depicts a cross-sectional view taken along section lines X-X of FIG. 8 in accordance with an illustrative embodiment.

With reference to FIG. 10, this figure depicts a cross-sectional view 1000 taken along section lines X-X of FIG. 8 in accordance with an illustrative embodiment. In the illustrated embodiment, the block arrows indicate directions of force applied to inner layers by the internal pressure point element 810 and the bottom cover 914. The internal pressure point element 810 is arranged to enhance contact reliability at interfaces of the diagnostic element 818A and distribution substrates 916A and 916B along the flow path 1012 taken by liquid of a test sample 902. The test sample 902 travels through hydrophilic regions of the distribution substrates 916A and 916B to colorimetric type diagnostic element 818A, specifically to the hydrophilic channel 1006 of the diagnostic element 818A. Thus, it keeps the interfaces between these various components urged together to force the liquid to travel through the various components rather than leak out over or between layers.

Figure 11:
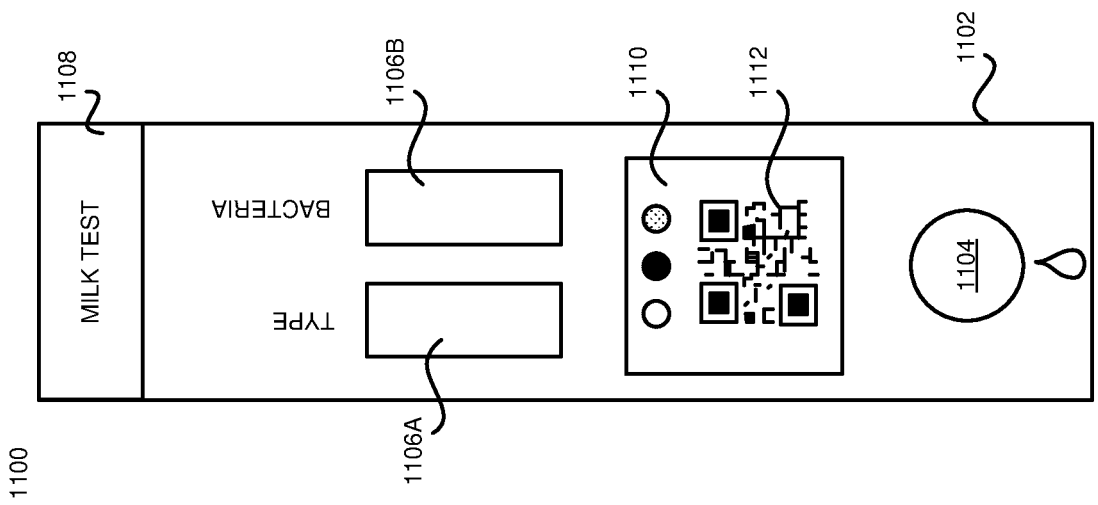
FIG. 11 depicts a plan view of a multiplexed rapid test device in accordance with an illustrative embodiment.

With reference to FIG. 11, this figure depicts a plan view of a multiplexed rapid test device 1100 in accordance with an illustrative embodiment. The test device 1100 includes a top cover 1102 having a sample receiving region 1104 and test result windows 1106A and 1106B. Embodiments of the disclosed test device may include a variety of graphical elements on outer surfaces, such as text, codes, and other indicia. For example, as shown in FIG. 11, graphical elements may include a test name 1108 indicating the type of test(s) performed by the multiplexed rapid test device 1100, color references 1110 and a QR code 1112 or other such graphical element that is encoded with information associated with one or more of the diagnostic elements. In some embodiments, the color references 1110 are provided for image processing to allow for machine-detection of the test results, for example an application on a smart phone or other such computing device that captures images of the test results and references 1110. In some embodiments, the application interprets the QR code for information, such as the type of test performed, the serial number of the test, lot number or other information. In some embodiments, the application stores the test results in a repository or database, such as a cloud-based storage, where it can later be retrieved and analyzed.

Figure 12:
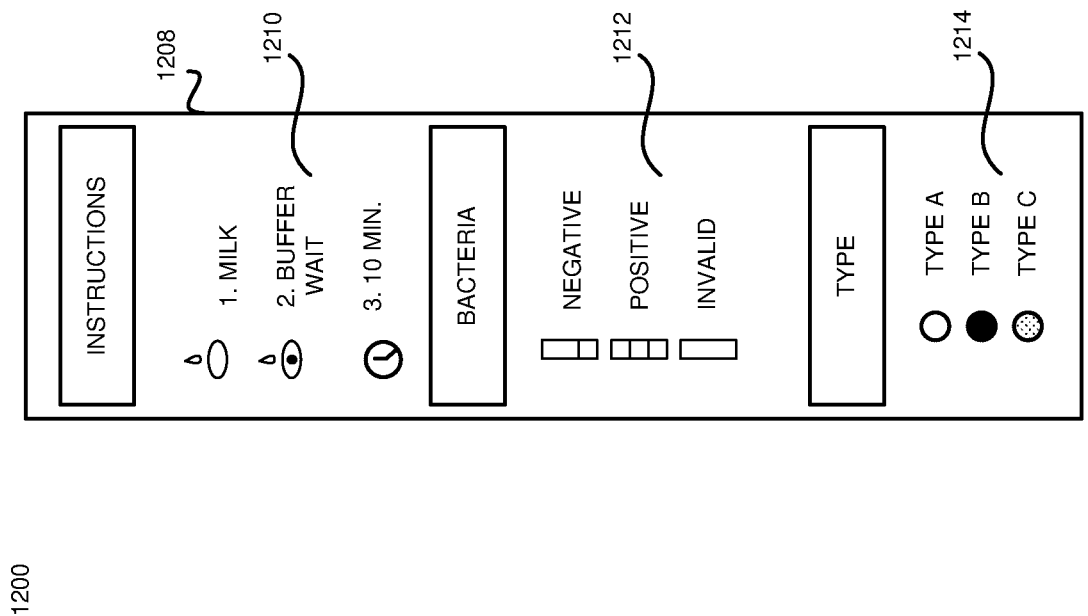
FIG. 12 depicts a plan view of a multiplexed rapid test device in accordance with an illustrative embodiment.

With reference to FIG. 12, this figure depicts plan view of a multiplexed rapid test device 1200 in accordance with an illustrative embodiment. The test device 1200 includes a bottom cover 1208. Embodiments of the disclosed test device may include a variety of graphical elements on outer surfaces, such as text, codes, and other indicia. For example, as shown in FIG. 12, graphical elements may include various messages for the user or consumer, such as instructions 1210 for using the test device, reference images 1212 for interpreting a first type of test performed by the test device 1200, and additional reference images 1214 for interpreting a second type of test performed by the test device 1200.

With reference to FIG. 13, this figure depicts an environment 1300 in which a mobile application is used with the multiplexed rapid test device 1100 in accordance with an illustrative embodiment. In the illustrated embodiment, a mobile device 1302 is used to capture an image 1304 of at least a portion of the multiplexed rapid test device 1100. However, in alternative embodiments, a tablet computer, laptop computer, or any known computing device equipped with a processor and one or more computer readable storage media, and program instructions collectively stored on the one or more computer readable storage media, the program instructions executable by the processor to cause the processor to perform operations including one or more of those described herein. For example, in some embodiments, the operations include capturing an image of a housing that includes a graphical element (e.g., such as test result windows 1106A and 1106B, color references 1110, and QR code 1112. In some embodiments, the operations include executing at least one data processing function on the captured image, wherein the data processing function comprises comparing a color attributes at a readout region in the captured image to color references in the captured image to determine at least one chemical attribute of a test sample.

A computer readable storage medium as used herein, including computer readable storage media as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

In the illustrated embodiment, the mobile device 1302 is running an application specifically for imaging test devices, such as multiplexed rapid test device 1100. In some embodiments, the mobile device 1302 runs an application that allows the user to capture an image of one or more graphical elements on outer surfaces of test devices. For example, in the illustrated embodiment, the mobile device 1302 runs an application that allows the user to instruct the mobile device 1302 to utilizes the camera technology of the mobile device 1110 to capture an image of test result windows 1106A and 1106B, color references 1110, and QR code 1112. In some embodiments, the mobile device 1302 evaluates the images of the test result windows 1106A and 1106B by comparing the colors of the stripes in test result windows 1106A and 1106B to the colors of the color references 1110 to determine the results of the tests. In the illustrated embodiment, the multiplexed rapid test device 1100 includes two colorimetric types of tests, but can include other types of tests in alternative embodiments. In some embodiments, the mobile device 1302 evaluates the image of the QR code 1112 by decoding the QR code 1112 to extract a network location (e.g., URL or IP address) of a cloud application or cloud storage device. In some such embodiments, the mobile device 1302 sends the test results to the network location encoded in the QR code 1112 for storage and/or for further processing of the test results. In some embodiments, the mobile device 1302 also extracts and displays and/or sends data features from the mobile device with the test results, such as a geographical location of the analyzed sample, a timestamp of when the analysis was performed on the sample, and/or the user who performed the chemical analysis.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "illustrative" is used herein to mean "serving as an example, instance or illustration." Any embodiment or design described herein as "illustrative" is not necessarily to be construed as preferred or advantageous over other embodiments or designs. The terms "at least one" and "one or more" are understood to include any integer number greater than or equal to one, i.e., one, two, three, four, etc. The terms "a plurality" are understood to include any integer number greater than or equal to two, i.e., two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. An apparatus comprising:
   a sample receiving region;
   a first diagnostic element that includes one or more colorimetric analysis regions;
   a second diagnostic element that includes one or more lateral flow assay analysis regions;
   a first distribution substrate comprising a first hydrophilic region and a first hydrophobic region that defines a boundary of the first hydrophilic region, wherein the first hydrophilic region receives liquid deposited at the sample receiving region; and
   a second distribution substrate comprising a second hydrophilic region that receives a first portion of liquid from the first hydrophilic region and allows the liquid to flow to the first diagnostic element, a third hydrophilic region that receives a second portion of liquid from the first hydrophilic region and is configured to allow the liquid to flow to the second diagnostic element, and a second hydrophobic region that is configured to oppose traversal of liquid from the second hydrophilic region to the third hydrophilic region.

2. The apparatus of claim 1, further comprising an impermeable housing, wherein the sample receiving region comprises an opening defined by the housing.

3. The apparatus of claim 2, further comprising a graphical element on the housing, wherein the graphical element is encoded with information associated with the first diagnostic element and the second diagnostic element.

4. The apparatus of claim 1, wherein the first diagnostic element comprises a sample conveying portion that guides the first portion of the liquid to a colorimetric reacting region.

5. The apparatus of claim 4, wherein each of the one or more colorimetric analysis regions comprises a first colorimetric reaction area, a second colorimetric reaction area, and a hydrophobic area that at least partially disposed between the first colorimetric reaction area and the second colorimetric reaction area.

6. The apparatus of claim 1, further comprising a pressure point element facilitating fluid communication between the first hydrophilic region and the first and second diagnostic regions.

* * * * *